US006891965B2

(12) United States Patent
Tanaka

(10) Patent No.: US 6,891,965 B2
(45) Date of Patent: May 10, 2005

(54) IMAGE DISPLAY METHOD AND APPARATUS

(75) Inventor: Nobuyuki Tanaka, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 587 days.

(21) Appl. No.: 09/986,693

(22) Filed: Nov. 9, 2001

(65) Prior Publication Data

US 2002/0061128 A1 May 23, 2002

(30) Foreign Application Priority Data

Nov. 21, 2000 (JP) ...................................... 2000-353864

(51) Int. Cl.[7] ................................................ G06K 9/00

(52) U.S. Cl. ...................... 382/132; 382/299; 382/274; 345/89; 345/690

(58) Field of Search ................................ 382/132, 274, 382/299; 128/922; 250/363.01, 363.02, 363.04, 582, 583; 378/4, 21; 377/10; 356/39; 345/690, 89, 699; 600/443; 358/1.9

(56) References Cited

U.S. PATENT DOCUMENTS 5,245,445 A * 9/1993 Fujisawa ................... 358/3.15
5,539,432 A * 7/1996 Kobayashi .................. 345/600
5,732,705 A * 3/1998 Yokoyama et al. ......... 600/443
5,796,865 A * 8/1998 Aoyama et al. ............ 382/169
6,134,351 A * 10/2000 Waki et al. ................ 382/252
6,198,837 B1 * 3/2001 Sasano et al. .............. 382/132
6,690,490 B1 * 2/2004 Murakami .................. 358/1.9
6,781,603 B2 * 8/2004 Tanaka ....................... 345/690
6,801,647 B1 * 10/2004 Arakawa .................... 382/132
2001/0021041 A1 * 9/2001 Suzuki ....................... 358/458
2002/0114504 A1 * 8/2002 Shinbata ..................... 382/132
2002/0167647 A1 * 11/2002 Numakoshi .................. 353/31

FOREIGN PATENT DOCUMENTS

JP 3-277357 A * 12/1991
JP 4-187142 A * 7/1992
JP 5-168622 A * 7/1993
JP 2976196 * 10/1999
JP 3038407 3/2000 ........... G03B/42/02

* cited by examiner

*Primary Examiner*—Bhavesh M. Mehta
*Assistant Examiner*—Barry Choobin
(74) *Attorney, Agent, or Firm*—Sughrue Mion, PLLC

(57) ABSTRACT

An image display apparatus which can always display images in proper gradation in the process of receiving image data and successively displaying images. The image display apparatus includes: a data receiving unit for successively receiving a plurality of pixel data representing an image; an image data generating unit for generating image data representing a picture on the basis of the pixel data, which has been received and represents a part of the picture, at predetermined intervals; an average value calculating unit for obtaining a quantity relevant to gradation of the picture; a look-up table altering unit for altering gradation processing condition of the image data on the basis of the quantity relevant to gradation; an image processing unit for executing gradation processing of the image data, in accordance with the gradation processing condition; and a display unit for displaying the picture by using the image data.

14 Claims, 5 Drawing Sheets

1
IMAGE DISPLAY APPARATUS
DATA RECEIVING UNIT
10
IMAGE DATA GENERATING UNIT
11
AVARAGE VALUE CALCULAING UNIT
12
LUT ALTERING UNIT
13
LUT
14
IMAGE PROCESSING UNIT
15
IMAGE DISPLAY UNIT
16
IMAGE READING APPARATUS
2
N1

IMAGE DISPLAY METHOD AND APPARATUS

BACKGROUND OF THE INVENTION

1. Field of the Invention

The present invention relates to an image display method of displaying images obtained by radiography and so on, and relates to an image display apparatus using the same.

2. Description of a Related Art

Photography using radiation (X-rays, $\alpha$-rays, $\beta$-rays, $\gamma$-rays, electron rays, ultraviolet rays and so on) has hitherto been used in a variety of fields, and especially in the medical field it becomes one of indispensable measures for diagnoses. X-ray radiography has had a lot of improvements since its first realization and now combining fluorescent screen and X-ray film is the mainstream. On the other hand, with various digitalized apparatuses such as X-ray CT, ultrasonic diagnosis, MRI and so on realized in recent years, diagnostic information processing systems are being structured in hospitals. With a lot of researches conducted to digitize X-ray images, radiography using photostimulable phosphor has been established and put into practical use to replace X-ray radiography.

Photostimulable phosphor (accumulative phosphor) is such a substance as follows. That is, the substance accumulates a part of the radiation energy when radiation is irradiated. After that, when excitation light such as visible light and so on is irradiated, the substance radiates photostimulated luminescence light in accordance with the accumulated energy. Existence of photostimulable phosphor has been known so far. The radiography using photostimulable phosphor is as follows. That is, a radiation image of an object like a human body is photographed and recorded on a sheet coated with photostimulable phosphor. Since photostimulated luminescence light is produced when the photostimulable phosphor sheet is scanned by excitation light such as a laser beam and so on, image data can be obtained by reading the light photo-electrically. After proper processing of the image data, a radiation image can be shown as a visible image on a display such as a CRT or on a film printed by a laser printer and so on.

The radiography compares with the conventional X-ray radiography in photographic sensibility and image quality. For example, compared with the conventional X-ray radiography, an exposure area is exceedingly wide and a response of photostimulated luminescence light is almost in proportion to an exposure amount in all the exposure area. Therefore, even if an object is photographed by any amount of radiation, image signals having proper gradation can be obtained by finding the luminous area of the image and normalizing it. Also, with a proper process of image signals obtained by this way, the image having good quality can be produced under a variety of photographing condition. Moreover, it is possible to store a lot of image data set for a long time without deterioration of image quality because the image by this radiophotography can be stored as digitized data. Such a system storing images as image data sets will be useful to the development of medical diagnostic information system.

In the conventional medical radiography system using the photostimulable phosphor sheet, a radiation image is photographed on photostimulable phosphor sheet, after that, image data representing the radiation image recorded on the sheet is read through a reading apparatus. Then, a whole of the read image data is read into a processing unit included in an image processing apparatus or an image display apparatus, and then, the image data is performed processing operation. So that, such a system has a defect of taking long time to display the visible image since the system reads the image data.

To judge the quality of photography, it is important to display a visible image soon and check it. Then, it is possible to save trouble of photographing again when, for example, mistake of photographing is made. Therefore, it is required to display high quality images as soon as possible.

Japanese Patent No. 3038407 discloses a radiation image information reading apparatus which writes linear gradation processing condition into a look-up table for display use and displays an image on the basis of image data by using the look-up table for display use in response to reading of a radiation image. After that, the apparatus obtains gradation processing condition corresponding to the radiation image on the basis of frequency distribution of the image data, writes the obtained gradation processing condition into the look-up table for display use, and alters an image to be displayed.

The look-up table is a conversion table used to alter received data value, and here, is used to rectify the gradation of the radiation image. The look-up table corresponding to photographing condition is made to reproduce gradation like that of film images on the basis of the received image data or reproduce photographed images in optimum gradation which differs with portions to be photographed.

The above-mentioned apparatus makes it possible to successively display an image while receiving the image data. However, in the apparatus, the image is not displayed in good gradation until all image data is received because the look-up table is fixed while the image is successively displayed, and altered by calculating optimum gradation when all image data is received, then the image is redisplayed. Therefore, the image is sometimes displayed in low density, that is, whitish or conversely, in high density, that is, blackish, which is improper to judge the quality of photography.

SUMMARY OF THE INVENTION

The present invention was accomplished in view of the above problems. An object of the present invention is to provide an image display method and apparatus which can always display images in proper gradation in the process of receiving image data and successively displaying images.

In order to achieve the above object, an image display method according to the present invention comprises the steps of: (a) successively receiving a plurality of pixel data representing an image; (b) generating image data representing a picture on the basis of the pixel data, which has been received and represents a part of the picture, at predetermined intervals; (c) obtaining a quantity relevant to gradation of the picture represented by the image data generated at step (b); (d) altering gradation processing condition of the image data on the basis of the quantity relevant to gradation obtained at step (c); (e) executing gradation processing of the image data generated at step (b) in accordance with the gradation processing condition altered at step (d); and (f) displaying the picture by using the image data obtained at step (e).

An image display apparatus according to the present invention comprises: first means for successively receiving a plurality of pixel data representing an image; second means for generating image data representing a picture on the basis of the pixel data, which has been received and represents a part of the picture, at predetermined intervals; third means for obtaining a quantity relevant to gradation of the picture represented by the image data generated by the second means; fourth means for altering gradation processing condition of the image data on the basis of the quantity relevant to gradation obtained by the third means; fifth means for executing gradation processing of the image data generated by the second means in accordance with the gradation processing condition altered by the fourth means; and sixth means for displaying the picture by using the image data obtained by the fifth means.

According to the present invention, the gradation processing condition is altered at predetermined intervals while image data is successively received, so that an image can successively be displayed in proper gradation at all times.

DESCRIPTION OF THE PREFERRED EMBODIMENTS

Figure 1:
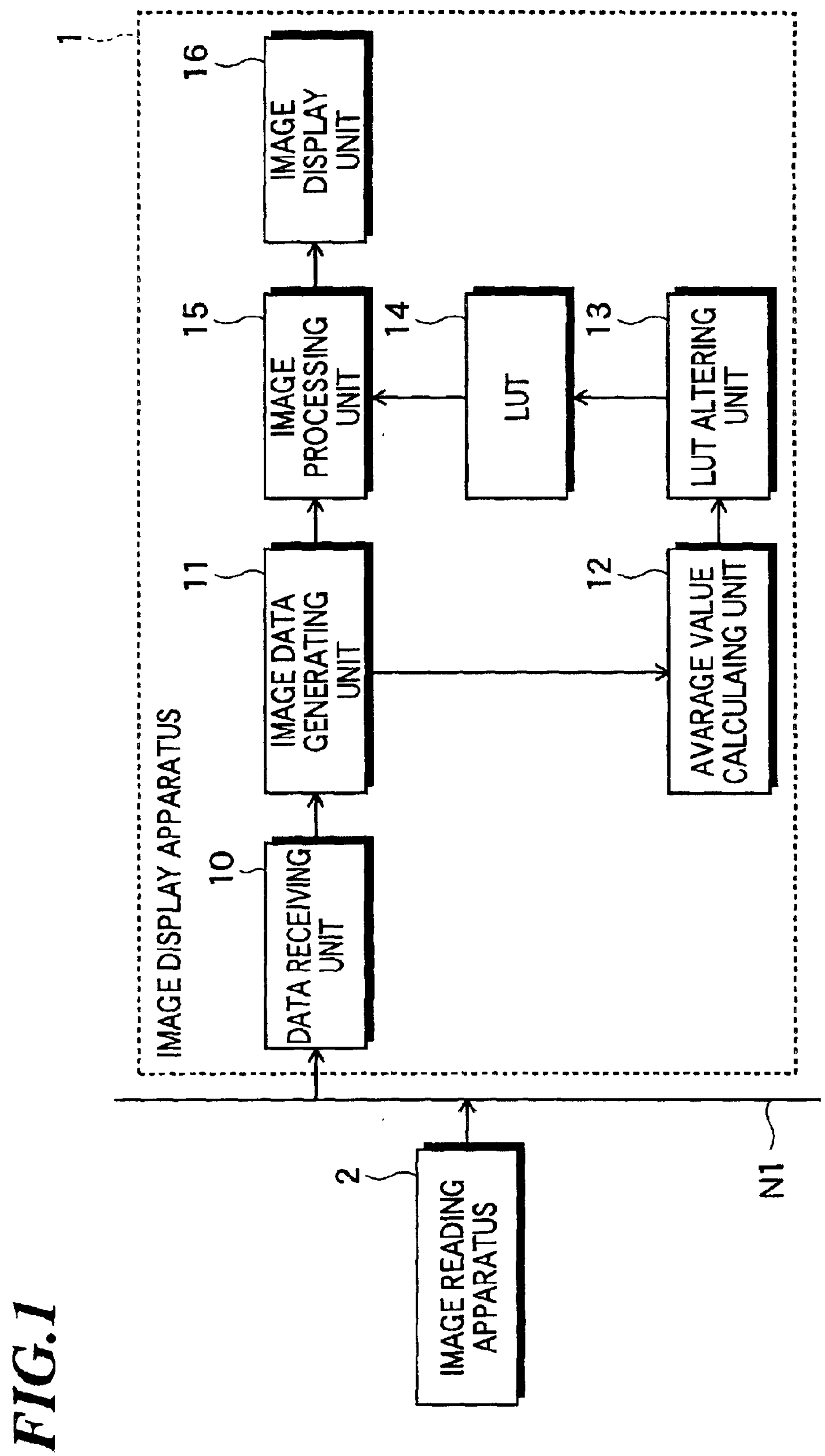
FIG. 1 is a block diagram showing a configuration of a medical image processing system including an image display apparatus according to one embodiment of the present invention.

Embodiments of the present invention will now be described in detail with reference to the drawings. The same constituent elements are designated by the same reference numerals and explanation thereof will be omitted.

FIG. 1 shows the configuration of a medical image processing system including an image display apparatus according to one embodiment of the present invention. A record sheet (a photostimulable phosphor sheet) for radiography is coated with photostimulable phosphor substance and records information of an object when the record sheet is irradiated by radiation.

In FIG. 1, an image display apparatus 1 and an image reading apparatus 2 are connected through the network N1. When image information is recorded on the record sheet by radiography, the image information is first read by the image reading apparatus 2, and the data generated from the read image information is transmitted into the image display apparatus 1.

Figure 2:
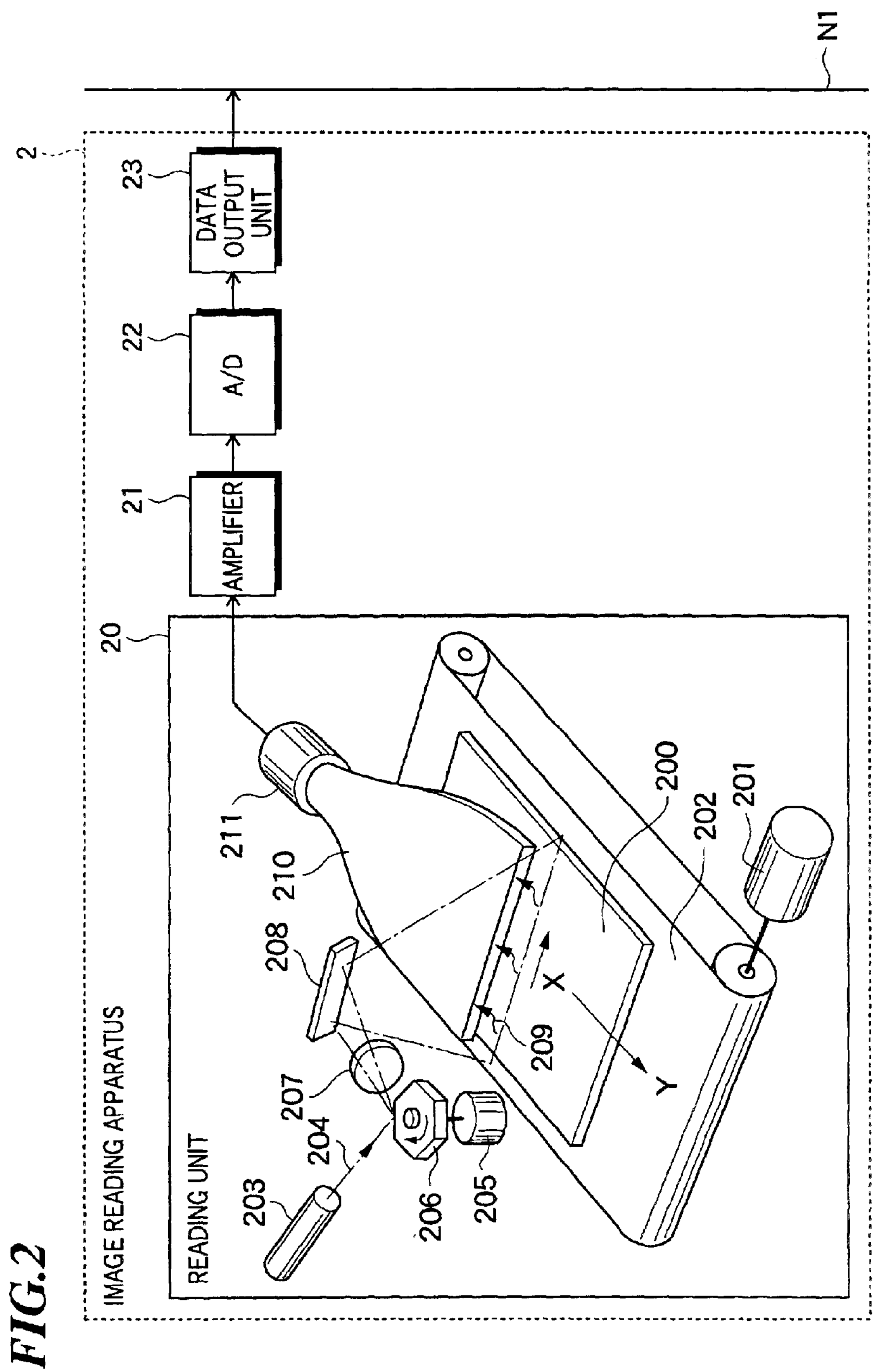
FIG. 2 is a diagram showing a configuration of an image reading apparatus included in the medical image processing system.

Next, the operation of the image reading apparatus 2 is explained in detail with reference to FIG. 2. In FIG. 2, a record sheet 200 for recording a radiation image is set at a predetermined place of the image reading apparatus. The record sheet 200 is carried in Y-direction by a sheet conveyance means 202 driven by a motor 201. On the other hand, a beam 204 generated from a laser light source 203 is reflected and deflected by a rotation polygon mirror 206 which driven by a motor 205 and turning at high speed in an arrow direction. Further the beam 204 passed through a convergence lens 207. After that, an optical path of the beam 204 is altered by a mirror 208, so that the beam 204 is incident upon the record sheet 200 and scanned in X-direction. The excitation light 204 is irradiated to the record sheet 200 by the scanning, and a photostimulated luminescence light 209 is generated from the irradiated site in accordance with accumulated and recorded radiation image information. The photostimulated luminescence light 209 is led by a light guide 210 and is photo-electrically detected by a photo multiplier 211. An analog signal output from the photo multiplier 211 is amplified by an amplifier 21 and digitized by an A/D converter 22. A data output unit 23 successively outputs the digitized image data into the image display apparatus 1 in FIG. 1 through a network N1.

Referring again to FIG. 1, a series of pixel data included in image data representing an image is successively transmitted into a data receiving unit 10 included in the image display apparatus 1. On the basis of the pixel data received by the data receiving unit 10, an image data generating unit 11 generates image data representing a whole picture and stores them. A look-up table (LUT) 14 stores gradation processing condition used to execute gradation processing of the image data and is set at an initial value just after reset or just before reception of the image data. An average value calculating unit 12 calculates an average value of predetermined pixel data as a quantity used to control the gradation processing of the image data generated by the image data generating unit 11. A look-up table altering unit 13 alters the look-up table 14 on the basis of the average value calculated by the average value calculating unit 12. An image processing unit 15 executes gradation processing of the image data generated by the image data generating unit 11 in accordance with the gradation processing condition stored in the look-up table 14, and also may perform various kinds of image processing. The image display unit 16 displays photographed images in optimum gradation on a display and the like on basis of the image data executed image processing.

Figure 3:
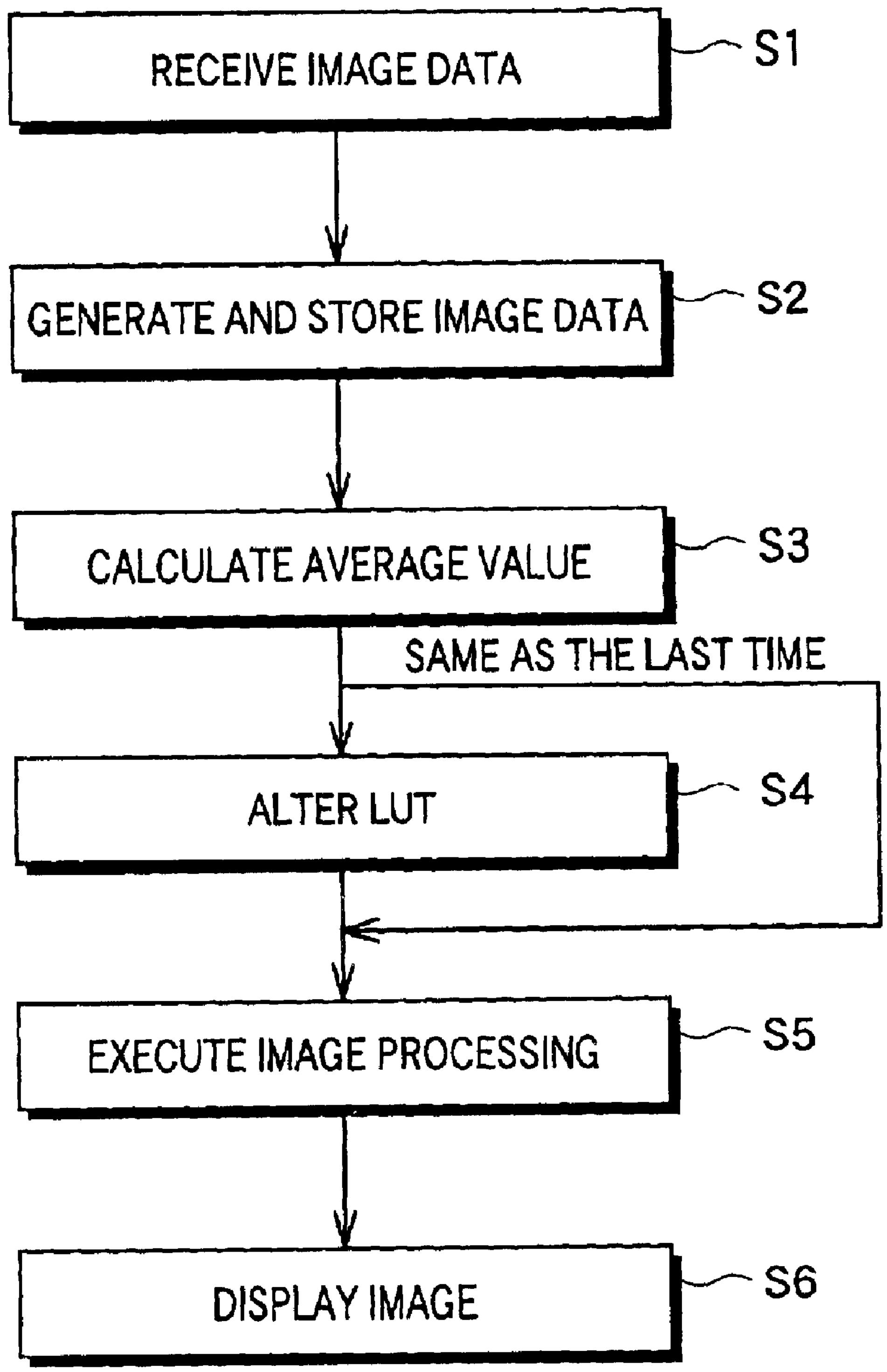
FIG. 3 is a flow chart representing an image display method according to one embodiment of the present invention.

The operation of the image display apparatus according to the embodiment will next be described in detail with reference to FIGS. 1 and 3. FIG. 3 is a flow chart representing the image display method according to the embodiment.

At step S1, image data representing a part of a picture is read by the reading apparatus and successively transmitted into the data receiving unit 10. Next, at step S2, the image data generating unit 11 generates image data representing a whole picture on the basis of the image data, which has been received before and represents a part of the picture, and stores them.

At step S3, the average value calculating unit 12 calculates an average value of predetermined pixel data included in the image data obtained by the image data generating unit 11. The calculated average value is normalized in the range of display density. The average value may be calculated by a pixel, a line unit or a block unit of the received pixel data. Although the average value is used as a characteristic value used to control gradation processing of the image data in the above explanation, a maximum value, a minimum value or the like may be used to determine the gradation processing condition.

Figure 4A:
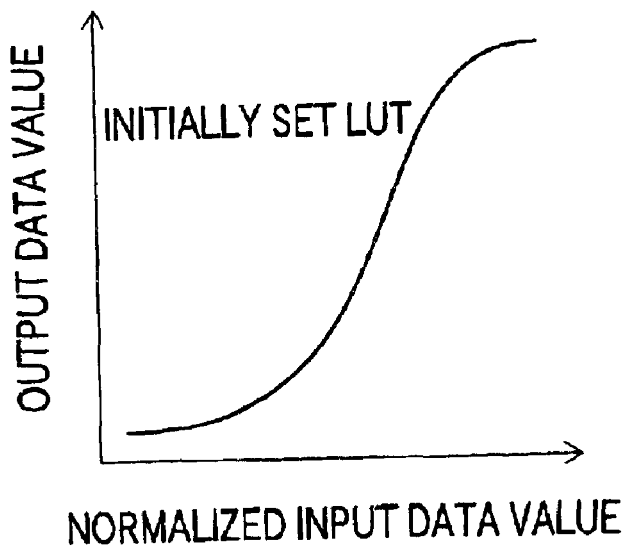
FIGS. 4A and 4B are graphs showing gradation characteristics, created on the basis of a look-up table.
Figure 4B:
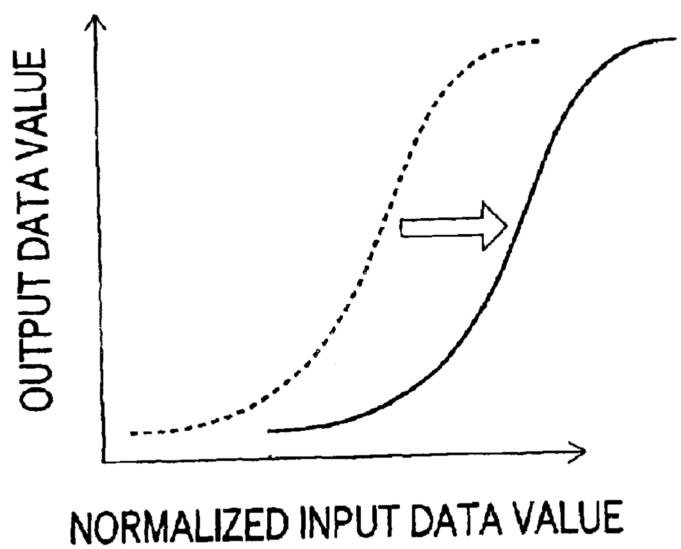

At step S4, the look-up table altering unit 13 alters the look-up table 14 on the basis of the above characteristic value. In the embodiment, the look-up table altering unit 13 translates the gradation processing condition (gradation characteristics) in parallel, which is set in the look-up table 14, in accordance with difference between predetermined optimum display brightness, such as a medium value of display density, and the above characteristic value, such as a normalized average value of the received pixel data. FIG. 4A indicates a gradation characteristics created on the basis of the initialized look-up table 14. The horizontal axis indicates normalized reception data values, and the vertical axis indicates output data values. First, a difference value between the normalized average value and the medium value of display density is calculated. For example, in the case of 8 bits display, since the medium value of the display density is 128, the difference value is calculated by subtracting 128 from the normalized average value. Next, as shown in FIG. 4B, the look-up table 14 is rewritten so that the curve indicating gradation characteristics on the basis of the initialized value may be translated in parallel as much as the difference value.

The look-up table may not be altered when the result of the calculation processing of the above average value by the average value calculating unit 12 is the same as that of the last time or included within the predetermined range.

At step S5, the image processing unit 15 executes gradation processing of the image data generated by the image data generating unit 11 by using the rewritten look-up table 14. At step S6, the image display unit 16 displays the image having optimum gradation.

Figure 5A:
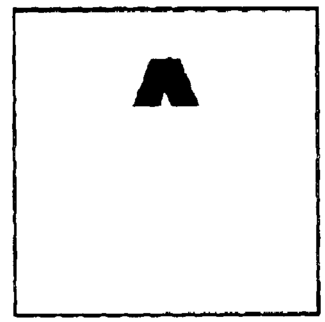
FIGS. 5A to 5C are diagrams showing pictures of an object displayed in succession.
Figure 5B:
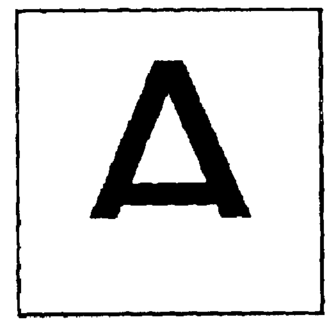
Figure 5C:
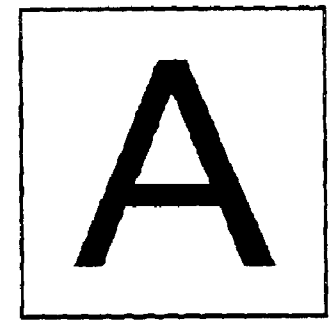

FIGS. 5A to 5C shows states of the successively displayed images. In FIG. 5A, an upper part of an object "A" appears in the picture. As shown in FIG. 5B, a displayed area of the object increases by repeating the processing operation successively. In the pictures as shown in FIGS. 5A and 5B, areas where the objects are still not displayed (lower parts of the pictures in FIGS. 5A and 5B) may be distinguished from the displayed object by setting brightness to be a maximum or minimum value. As shown in FIG. 5C, a whole image of the object is displayed while the processing is further advanced.

According to the embodiment, as shown in FIGS. 5A and 5B, even when only a part of an image is displayed, it is possible to display the image in proper gradation in respective stages by altering the look-up table on the basis of image data made up with pixel data received until that time. Therefore, the clear image that makes it possible to judge the quality of photography can be obtained even when only a part of the image is displayed in the picture.

Both analog and digital circuits may be used for constituting the image data generating unit 11, the average value calculating unit 12, the look-up table altering unit 13 and the image processing unit 15 as shown in FIG. 1. Alternatively, a combination of a central processing unit (CPU) and software may be also used for constituting them. In this case, the software is recorded on a recording medium such as a hard disk, a floppy disk, MO, MT, CD-ROM, DVD-ROM and so on. The look-up table 14 may be constituted with a temporary storage medium such as a random access memory (RAM) and so on. The image display unit 16 may include a display such as a CRT and so on.

Although the network connects the image reading apparatus and the image display apparatus in FIG. 1, it is possible to directly connect the image reading apparatus and the image display apparatus, and directly transmit the image data read by a scanner into the image display apparatus.

As described above, according to the present invention, since the look-up table is dynamically altered successively on the basis of pixel data successively received, it is always possible to display an image in proper gradation at each time when the pixel data is received. It is, therefore, possible to judge the quality of photography easily even while the pixel data is being received.

What is claimed is:

1. An image display method comprising the steps of:

(a) successively receiving a plurality of pixel data representing an image;

(b) generating image data representing a picture on the basis of the pixel data, which has been received and represents a part of the picture, at predetermined intervals;

(c) obtaining a quantity relevant to gradation of the picture represented by the image data generated at step (b);

(d) altering gradation processing condition of the image data on the basis of the quantity relevant to gradation obtained at step (c);

(e) executing gradation processing of the image data generated at step (b) in accordance with the gradation processing condition altered at step (d); and (f) displaying the picture by using the image data obtained at step (e).

2. An image display method according to claim 1, wherein step (a) includes successively receiving the plurality of pixel data through a network.

3. An image display method according to claim 1, wherein step (a) includes successively receiving the plurality of pixel data representing an image photographed by radiography and read by a scanner.

4. An image display method according to claim 1, wherein step (c) includes obtaining the quantity relevant to gradation of the picture by using an average value of the pixel data received at step (a).

5. An image display method according to claim 1, wherein steps (b) and (c) are repeated by one of a pixel unit, a line unit and a block unit.

6. An image display method according to claim 1, wherein step (d) includes translating the gradation processing condition in parallel, which has been initially set in a look-up table, in accordance with difference between predetermined display brightness and the quantity relevant to gradation obtained at step (c).

7. An image display method according to claim 1, wherein, when the quantity relevant to gradation obtained at step (c) is within a predetermined range from the quantity relevant to gradation obtained at the last time, the gradation processing condition set in the look-up table is not altered at step (d).

8. An image display apparatus comprising:

first means for successively receiving a plurality of pixel data representing an image;

second means for generating image data representing a picture on the basis of the pixel data, which has been received and represents a part of the picture, at predetermined intervals;

third means for obtaining a quantity relevant to gradation of the picture represented by the image data generated by said second means;

fourth means for altering gradation processing condition of the image data on the basis of the quantity relevant to gradation obtained by said third means;

fifth means for executing gradation processing of the image data generated by said second means in accordance with the gradation processing condition altered by said fourth means; and sixth means for displaying the picture by using the image data obtained by said fifth means.

9. An image display apparatus according to claim 8, wherein said first means successively receives the plurality of pixel data through a network.

10. An image display apparatus according to claim 8, wherein said first means successively receives the plurality of pixel data representing an image photographed by radiography and read by a scanner.

11. An image display apparatus according to claim 8, wherein said third means obtains the quantity relevant to gradation of the picture by using an average value of the pixel data received by said first means.

12. An image display apparatus according to claim 8, wherein:

said second means generates the image data by one of a pixel unit, a line unit and a block unit; and said third means obtains the quantity relevant to gradation of the picture by one of the pixel unit, the line unit and the block unit.

13. An image display apparatus according to claim 8, wherein said fourth means translates the gradation processing condition in parallel, which has been initially set in a look-up table, in accordance with difference between predetermined display brightness and the quantity relevant to gradation obtained by said third means.

14. An image display apparatus according to claim 8, wherein, when the quantity relevant to gradation obtained by said third means is within a predetermined range from the quantity relevant to gradation obtained at the last time, the gradation processing condition set in the look-up table is not altered by said fourth means.

* * * * *